(12) United States Patent
Borden et al.

(10) Patent No.: US 9,506,027 B2
(45) Date of Patent: Nov. 29, 2016

(54) MICROBUBBLE DEVICES, METHODS AND SYSTEMS

(71) Applicant: The Trustees of Columbia University in the City of New York, New York, NY (US)

(72) Inventors: Mark A. Borden, Boulder, CO (US); Eric G. Lima, Patterson, NY (US); Clark T. Hung, Ardsley, NY (US); Shashank Ramesh Sirsi, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 377 days.

(21) Appl. No.: 14/087,276

(22) Filed: Nov. 22, 2013

(65) Prior Publication Data
US 2014/0141500 A1    May 22, 2014

Related U.S. Application Data

(62) Division of application No. 13/393,273, filed as application No. PCT/US2010/047263 on Aug. 31, 2010, now Pat. No. 8,617,892.

(60) Provisional application No. 61/304,782, filed on Feb. 15, 2010, provisional application No. 61/239,000, filed on Sep. 1, 2009.

(51) Int. Cl.
| | |
|---|---|
| *C12N 5/00* | (2006.01) |
| *C12N 5/02* | (2006.01) |
| *C12M 1/36* | (2006.01) |
| *C12N 5/077* | (2010.01) |

(52) U.S. Cl.
CPC ............ *C12M 41/48* (2013.01); *C12N 5/0655* (2013.01); *C12N 2533/76* (2013.01)

(58) Field of Classification Search
None
See application file for complete search history.

(56) References Cited

U.S. PATENT DOCUMENTS

| | | |
|---|---|---|
| 3,598,111 A | 8/1971 | Kahn et al. |
| 4,777,599 A | 10/1988 | Dorogi et al. |
| 5,107,837 A | 4/1992 | Ophir et al. |
| 5,178,147 A | 1/1993 | Ophir et al. |
| 5,309,914 A | 5/1994 | Iinuma |
| 5,435,310 A | 7/1995 | Sheehan et al. |
| 5,601,084 A | 2/1997 | Sheehan et al. |
| 5,606,971 A | 3/1997 | Sarvazyan |

(Continued)

FOREIGN PATENT DOCUMENTS

| | | |
|---|---|---|
| WO | WO 2010/044385 | 4/2010 |
| WO | WO 2010/063951 | 6/2010 |

OTHER PUBLICATIONS

Gotoh et al., Cytotech., 11:35-40 (1993).*

(Continued)

*Primary Examiner* — Thomas J Visone
(74) *Attorney, Agent, or Firm* — Potomac Law Group, PLLC; Mark Catan

(57) ABSTRACT

A hydrogel tissue engineering scaffold having microbubbles dispersed therein is disclosed. Also, a system for cell culturing including a controller and actuator to apply dynamic deformational loading to a hydrogel is disclosed. Also disclosed are methods for producing hydrogels with microbubbles and for culturing cells using hydrogels with microbubbles.

6 Claims, 15 Drawing Sheets

(56) References Cited

U.S. PATENT DOCUMENTS

| | | |
|---|---|---|
| 5,662,113 A | 9/1997 | Liu |
| 5,722,411 A | 3/1998 | Suzuki et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,102,864 A | 8/2000 | Hatfield et al. |
| 6,102,865 A | 8/2000 | Hossack et al. |
| 6,123,669 A | 9/2000 | Kanda |
| 6,210,611 B1 | 4/2001 | Needham et al. |
| 6,241,675 B1 | 6/2001 | Smith et al. |
| 6,245,318 B1 | 6/2001 | Klibanov et al. |
| 6,246,895 B1 | 6/2001 | Plewes |
| 6,312,382 B1 | 11/2001 | Mucci et al. |
| 6,352,507 B1 | 3/2002 | Torp et al. |
| 6,508,768 B1 | 1/2003 | Hall et al. |
| 6,537,217 B1 | 3/2003 | Bjærum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu |
| 6,703,047 B2 | 3/2004 | Sawhney et al. |
| 6,875,176 B2 | 4/2005 | Mourad et al. |
| 7,055,378 B2 | 6/2006 | Su et al. |
| 7,257,244 B2 | 8/2007 | Miga |
| 7,331,926 B2 | 2/2008 | Varghese et al. |
| 7,421,101 B2 | 9/2008 | Georgescu et al. |
| 7,601,122 B2 | 10/2009 | Zagzebski et al. |
| 7,753,847 B2 | 7/2010 | Greenleaf et al. |
| 8,029,444 B2 | 10/2011 | Pedrizzetti et al. |
| 2002/0065461 A1 | 5/2002 | Cosman |
| 2003/0220556 A1 | 11/2003 | Porat et al. |
| 2004/0006266 A1 | 1/2004 | Ustuner et al. |
| 2004/0059224 A1 | 3/2004 | Varghese et al. |
| 2004/0092816 A1 | 5/2004 | Ossmann et al. |
| 2004/0249580 A1 | 12/2004 | Pourcelot et al. |
| 2005/0004466 A1 | 1/2005 | Hynynen et al. |
| 2005/0054930 A1 | 3/2005 | Rickets et al. |
| 2005/0059876 A1 | 3/2005 | Krishnan et al. |
| 2005/0080336 A1 | 4/2005 | Byrd et al. |
| 2005/0260189 A1 | 11/2005 | Klibanov et al. |
| 2005/0267695 A1 | 12/2005 | German |
| 2006/0058673 A1 | 3/2006 | Aase et al. |
| 2006/0074315 A1 | 4/2006 | Liang et al. |
| 2006/0173320 A1 | 8/2006 | Radulescu |
| 2007/0049824 A1 | 3/2007 | Konofagou et al. |
| 2007/0219447 A1 | 9/2007 | Kanai et al. |
| 2007/0276242 A1 | 11/2007 | Konofagou |
| 2007/0276245 A1 | 11/2007 | Konofagou |
| 2008/0194957 A1 | 8/2008 | Hoctor et al. |
| 2008/0269606 A1 | 10/2008 | Matsumura |
| 2008/0285819 A1 | 11/2008 | Konofagou et al. |
| 2009/0123435 A1 | 5/2009 | Ratcliffe et al. |
| 2010/0166668 A1 | 7/2010 | Wei et al. |
| 2011/0208038 A1 | 8/2011 | Konofagou et al. |

OTHER PUBLICATIONS

Nair et al., Tiss. Eng., 16(1):23-32 (2010).*
Nair, Thesis, 2006.*
Eiselt et al., Biomater., 21:192-1927 (2000).*
Avolio et al., "Effects of aging on changing arterial compliance and left ventricular load in a northern Chinese urban community," Circulation, vol. 68(1), pp. 50-58, 1983.
Badke et al., (1980) "Effects of ventricular pacing on regional left ventricular performance in the dog," Am J Physiol Heart Circ Physiol 238:H858-867.
Bercoff et al., "Supersonic Shear Imaging: A new technique for soft tissue elasticity mapping," IEEE Transactions on Ultrasonics, Ferroelectrics, and Frequency Control, vol. 51(4), pp. 396-409, Apr. 2004.
Berger et al., (2006) "Single-Beat Noninvasive Imaging of Cardiac Electrophysiology of Ventricular Pre-Excitation. Journal of the American College of Cardiology," 48(10):2045-2052.
Bers, D.M., "Cardiac excitation-contraction coupling", Nature, Jan. 10, 2002, vol. 415:198-205.
Bonnefous et al., "Time domain formulation of pulse-Doppler ultrasound and blood velocity estimation by cross-correlation," Ultrason Imaging, vol. 8(2), pp. 73-85, Apr. 1986.
Borden et al., "Ultrasound Radiation Force Modulates Ligand Availability on Target Contrast Agents," Mol. Imaging, 5:139-147 (2006).
Brooks et al., "Electrical Imaging of the Heart," IEEE Signal Processing Magazine, vol. 14(1), pp. 24-42, Jan. 1997.
Campbell et al., "Mechanisms of transmurally varying myocyte electromechanics in an integrated computational model," Phl. Trans. R. Soc. A., 366:3361-3380, Jul. 1, 2008.
Chen et al., "Radiation-force-based estimation of acoustic attenuation using harmonic motion imaging," Sep. 2012, p. 1983 in "Biomedical Acoustics and Signal Processing in Acoustics: Measurement of Material Properties Using Wave Propagation Methods," *Journal of the Acoustical Society of America*, Sep. 2012, 3(2): pp. 1980-2018.
Cobbold, R.S.C., "Foundations of biomedical ultrasound," 2007, Biomedical engineering series, Oxford University Press, pp. 422-423.
Cutnell et al., Table of Contents for "Physics," Fourth Edition, 1998, New York.
Damianou et al., "Dependence of Ultrasonic Attenuation and absorption in dog soft tissues on Temperature and Thermal dose," The Journal of Acoustical Society of America, 102(1):628-634 (1997).
De Craene et al., "Temporal diffeomorphic free-form deformation: Application to motion and strain estimation from 3D echocardiography," Medical Image Analysis, 16(2):427-450 (2012).
Declerck et al., "Left ventricular motion reconstruction from planar tagged MR images: a comparison," Phys Med Biol, vol. 45(6), pp. 1611-1632, Jun. 2000.
DuBose et al., "Confusion and Direction in Diagnostic Doppler Sonography," Journal of Diagnostic Medical Sonography, 25(3):173-177 (2009).
Duck, F.A., Table of Contents for "Physical Properties of Tissue: A Comprehensive Reference Book," 1990, Academic Press Ltd., London, UK.
Duerinckx et al., "In vivo Acoustic Attentuation in Liver: Correlations with Blood Tests and Histology," Ultrasonic in Medicine & Biology, 14(5):405-413 (1988).
Durrer et al. (1970) "Total Excitation of the Isolated Human Heart." Circulation, 41:899-912.
Edwards et al., "Effects of Ischemia on Left-Ventricular Regional Function in the Conscious Dog," American Journal of Physiology, vol. 240, pp. H413-H420, 1981.
Extended European Search Report, dated May 6, 2014, for European Application No. 10838238.3.
Faris et al. (2003) "Novel Technique for Cardiac Electromechanical Mapping with Magnetic Resonance Imaging Tagging and an Epicardial Electrode Sock," Ann Biomed Eng. 31:430-440.
Fenster et al., "Three-dimensional ultrasound imaging," Physics in Medicine and Biology, 46(5):R67-R99 (2001).
Fujii et al., "A New Method for Attenuation Coefficient Measurement in the Liver," Journal of Ultrasound in Medicine, 21(7):783-788 (2002).
Fung, Y.C., Table of Contents for "Biomechanics—Mechanical Properties of Living Tissues," 1993, Springer-Verlag, New York.
Ginat et al., "High-resolution ultrasound elastography of articular cartilage in vitro," *Proceedings of the 28th IEEE EMBS Annual International Conference*, New York City, USApp. 6644-6647 (Aug. 30-Sep. 3, 2006).
Greenstein et al., (2006) "Mechanisms of Excitation-Contraction Coupling in an Integrative Model of the Cardiac Ventricular Myocyte," Biophysical Journal 90:77-91.
Greenwald, S.E., "Pulse pressure and arterial elasticity," QJM: An International Journal of Medicine, vol. 95(2), pp. 107-112, 2002.
Gupta et al., "Changes in Passive mechanical Stiffness of Myocardial Tissue with Aneurysm Formation," Circulation, vol. 89, pp. 2315-2326, 1994.

(56) References Cited

OTHER PUBLICATIONS

Gurev et al., "Distribution of Electromechanical Delay in the Heart: Insights from a Three-Dimensional Electromechanical Model," Biophysical Journal 99:745-754, Aug. 2010.
Gurev et al., "In silico characterization of ventricular activation pattern by electromechanical wave imaging," Poster Session 5, PO05-80, Supplement to Heart Rhythm 6: p. S357.
Heimdal et al., "Real-time strain rate imaging of the left ventricle by ultrasound," J Am Soc Echocardiog, vol. 11(11), pp. 1013-1019, 1998.
Henderson et al., "Series Elasticity of Heart Muscle During Hypoxia," Cardiovascular Research, vol. 5, pp. 10-14, 1971.
Housden et al., "Ultrasonic imaging of 3D displacement vectors using a simulated 2D arrary and beamsteering," Ultrasonics, 53(2):615-621 (2013).
Huang et al., "Watershed Segmentation for Breast Tumor in 2-D Sonography," May 2004, Ultrasound in Medicine and Biology, pp. 625-632.
International Search Report for International Application No. PCT/US11/34704, dated Aug. 18, 2011.
Jasaityte et al., "Current state of three dimensional myocardial strain estimation using echocardiography," Journal of the American Society of Echocardiography, 26(1):15-28 (2013).
Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.
Kallel et al., "A least-squares strain estimator for elastography," Ultrasonic Imaging, 1997, 19:195-208.
Kanai et al., "A New Method for Measuring Small Local Vibrations in the Heart Using Ultrasound," IEEE T Bio-Med Eng, vol. 40(12), pp. 1233-1242, Dec. 1993.
Kanai et al., "Myocardial rapid velocity distribution," Ultrasound Med. & Biol., vol. 27(4), pp. 481-498, Apr. 2001.
Kanai et al., "Transcutaneous measurement of frequency dispersion in the regional pulse wave velocity," IEEE Ultrasonics Symposium, 2000.
Kanai, H., "Propagations of spontaneously actuated pulsive vibration in human heart wall and in vivo viscoelasticity estimation," IEE Transaction on Ultrasonics, Ferroelectrics, and Frequency Control, vol. 52(11), pp. 1931-1942, Nov. 2005.
Kimber et al. (1996) "A Comparison of Unipolar and Bipolar Electrodes During Cardiac Mapping Studies," Pacing Clin Electro 19:1196-1204.
Konofagou et al., "A New Elastographic Method for Estimation and Imaging od Lateral Strains, Corrected Axial Strains and Poisson's Ratios in Tissues," Ultrasound in Medicine & Biology 24(8): 1183-1199, 1998.
Konofagou et al., "Electromechanical Wave imaging for noninvasive mapping of the 3D electrical activation sequence in canines and humans in vivo," Journal of Biomechanics, 45(5):856-864 (Mar. 15, 2012).
Konofagou et al., "Myocardial Elastography—Feasibility Study in Vivo," Ultrasound Med & Biol, vol. 28(4), pp. 475-482, Apr. 2002.
Konofagou et al., "Noninvasive Electromechanical Wave Imaging and Conduction Velocity Estimation In Vivo," Ultrasonics Symposium, 2007 IEEE, pp. 969-972, 2007.
Konofagou et al., "Noninvasive electromechanical wave imaging and conduction-relevant velocity estimation in vivo," Ultrasonics,50(2):208-215 (2010).
Konofagou et al., "Three-dimensional Motion estimation in Elastography," IEEE Proceedings of the Symposium of Ultrasonics, Ferroelectrics, and Frequency Control in Sendai Japan, pp. 1745-1748, vol. 2, 1998.
Konofagou et al., "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Lai et al., Table of Contents for "Introduction to Continuum Mechanics," Third Edition, 1993, Pergamon Press, New York.

Lee et al., "Theoretical Quality Assessment of Myocardial Elastography with In Vivo Validation," Ultrasonics, Ferroelectrics and Frequency Control, IEEE Transactions on 54(1):2233-2245, Nov. 11, 2007.
Luo et al., "A fast normalized cross-correlation method for motion estimation," IEEE Trans. Ultrason. Ferroelectr. Control 57(6): 1347-1357, Jun. 2010.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Luo et al., "Myocardial elastography at both high temporal and spatial resolution for the detection of infarcts," Ultrasound in Med. & Bio, vol. 33(8), pp. 1206-1223, Aug. 2007.
Luo et al., "Pulse wave imaging of normal and aneurysmal abdominal aortas in vivo", IEEE Trans. Med. Imaging 28(4): 477-486, 2009.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Maleke et al., "Single-Element focused Ultrasound Transducer Method for Harmonic Motion Imaging," Ultrason. Imagin, vol. 28, No. 3, pp. 144-158, 2006.
McLaughlin et al., "Piezoelectric sensor determination of arterial pulse wave velocity," Physiol. Meas., vol. 24(3), pp. 693-702, 2003.
Mitri et al., "Chirp imaging vibro-acoustography for removing the ultrasound standing wave artifact," IEEE transactions on medical imaging, vol. 24(10), pp. 1249-1255, Oct. 2005.
Nichols et al., Table of Contents for "McDonald's blood flow in arteries: theoretic, experimental, and clinical principles," 4th Edition, 1998, Oxford University Press, New York.
Ophir et al., "Elastography: A quantitative method for imaging the elasticity of biological tissues," Ultrasonic Imaging, vol. 13(2), pp. 111-134, 1991.
Otani et al., "Transmural ultrasound-based visualization of patterns of action potential wave propagation in cardiac tissue," Annals Biomedical Engineering, 38(10):3112-3123 (2010).
Otani et al., "Use of ultrasound imaging to map propagating action potential waves in the heart," Computers in Cardiology, 36:617-620 (2009).
Palmeri et al., "Characterizing Acoustic Attenuation of Homogeneous Media Using Focused Impulsive Acoustic Radiation Force," Ultrasonic Imaging, 28(2):114-128 (2006.
Papadakis, E.P., Table of Contents for "Ultrasonic Instruments & Devices: Reference for Modern Instrumentation, Techniques, and Technology," 1999, Academic Press, New York.
Pernot et al., "Electromechanical Imaging of the Myocardium at Normal and Pathological States", Ultrasonics Symposium, 2005 IEEE, pp. 1091-1094, 2005.
Pernot et al.,(2007) "ECG-gated, Mechanical and Electromechanical Wave Imaging of Cardiovascular Tissues in Vivo," Ultrasound in Medicine & Biology 33(7):1075-1085.
Prinzen et al., (1992) "The time sequence of electrical and mechanical activation during spontaneous beating and ectopic stimulation," Eur Heart J 13:535-543.
Provost et al., "In Vivo Validation of 2D Myocardial Elastography at Variable Levels of Ischemia," 2008 IEEE International Ultrasonics Symposium Proceedings, pp. 962-965.
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico-in vivo reciprocity study," Heart Rhythm, 8(5):752-759 (2011).
Provost et al., (2010) "Electromechanical Wave Imaging of Normal and Ischemic Hearts in Vivo," IEEE Trans. Med. Imaging 29(3):625-635.
Qin et al., "The Natural Frequency of Nonlinear Oscillation of Ultrasound Contrast Agents in Microvessels," Ultrasound in Med. & Biol., vol. 33, No. 7, pp. 1140-1148, 2007.

(56) References Cited

OTHER PUBLICATIONS

Ramanathan et al., "Activation and repolarization of the normal human heart under complete physiological conditions," Proceedings of the National Academy of Sciences 103(16):6309 -6314, Apr. 18, 2006.
Ramanathan et al., (2004) "Noninvasive electrocardiographic imaging for cardiac electrophysiology and arrhythmia," Nat Med 10(4):422-428.
Revell et al., "Computer Vision Elastography: Speckle Adaptive Motion Estimation for Elastography Using Ultrasound Sequences." IEEE Transactions on Medical Imaging, vol. 24, No. 6, pp. 755-766 (2005).
Rice et al., "Approximate model of cooperative activation and crossbridge cycling in cardiac muscle using ordinary differential equations," Biophys. J 95:2368-2390, Sep. 2008.
Rogers et al., "Age-associated changes in regional aortic pulse wave velocity," J Am Coll Cardiol, vol. 38(4), pp. 1123-1129, 2001.
Roth, B.J., "Influence of a perfusing bath on the foot of the cardiac action potential," Circulation Research, vol. 86, E19-E22, 2000.
Samuel et al., "An ex vivo study of the correlation between acoustic emission and microvascular damage," Ultrasound Med. Biol., vol. 35, No. 9, pp. 1574-1586, 2009.
Sandrin et al., "Time-resolved pulsed elastography with ultrafast ultrasonic imaging," Ultrason Imaging, vol. 21(4), pp. 259-272, 1999.
Sarvazyan et al., "Shear wave elasticity imaging: A new ultrasonic technology of medical diagnostics," Ultrasound Med Biol, vol. 24(9), pp. 1419-1475, Nov. 1998.
Scher et al., (1956) "The pathway of ventricular depolarization in the dog," Circ Res 4:461-469.
Sengupta et al.,(2008) "Electromechanical activation sequence in normal heart," Heart Fail Clin 4:303-14.
Shehata et al., (2009) "Myocardial tissue tagging with cardiovascular magnetic resonance," Journal of Cardiovascular Magnetic Resonance 11:55.
Shiina et al., "Real time tissue elasticity imaging using the combined autocorrelation method," *J. Med. Ultrasonics*, 29(autumn):119-128 (2002).
Sinkus et al., "High-resolution tensor MR elastography for breast tumour detection," Phys Med Biol, 2000, 45(6):1649-1664.
Spach et al., "Extracellular discontinuities in cardia muscle—Evidence for capillary effects on the action potential foot," Circulation Research, vol. 83, pp. 1144-1164, 1998.
Stewart et al., "Blood-eye barriers in the rat: Correlation of ultrastructure with function," J. Comp. Neurol., vol. 340, No. 4, pp. 566-576, 1994.
Sutherland, G.R., "Color Doppler Myocardial Imaging—Potential Applications in Acquired and Congential Heart Disease," Acta Paediatr Suppl. 410: pp. 40-48, Aug. 1995.
Tanter et al., "Ultrafast compound imaging for 2-D motion vector estimation: application to transient elastography," IEEE Trans Ultrason Ferroelectr Freq Control, vol. 49(10), pp. 1363-1374, 2002.
Techavipoo et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Techavipoo et al., "Temperature Dependence of Ultrasonic Propagation Speed and Attentuation in Excised Canine Liver Tissue Measured Using Transmitted and Reflected Pulses," The Journal of Acoustical Society of America, 115(6):2859-2865 (2004).
Vappou et al., "Quantitative Viscoelastic Parameters Measured by Harmonic Motion Imaging," Phys. Med. Biol., vol. 54, pp. 3579-3595, Mar. 2009.
"Vial" entry from Wikipedia [online] [retrieved on May 20, 2014]. Retrieved from the Internet <URL: http://en.wikipedia.org/wiki/Vial>.

Walker et al., "A Fundamental Limit on Delay Estimation Using Partially Correlated Speckle Signals," IEEE T Ultrason Ferr, vol. 42(2), pp. 301-308, Mar. 1995.
Walker et al., (1994) "A fundamental limit on the performance of correlation based phase correction and flow estimation techniques," Ultrasonics, Ferroelectrics and Frequency Control, IEEE Transactions on 41(5):644-654, Sep. 1994.
Wang et al., "A composite high frame-rate system for clinical cardiovascular imaging," IEEE Transactions on Ultrasonics, Ferroelectrics, and Frequency Control, vol. 55(10), pp. 2221-2233, Oct. 2008.
Wang et al., "A composite imaging technique for high frame-rate and full-view cardiovascular ultrasound and elasticity imaging," IEEE International Ultrasonics Symposium, New York, NY, Oct. 28-31, 2007.
Wang et al., "Increased aortic stiffness assessed by pulse wave velocity in apolipoprotein E-deficient mice," Am J Physiol Heart Circ Physiol, vol. 278, No. 2, pp. H428-H434, 2000.
Wyman et al., (1999) "Mapping propagation of mechanical activation in the paced heart with MRI tagging," Am J Physiol Heart Circ Physiol 276:H881-891.
Yuh et. al., "Delivery of Systemic Chemotherapeutic Agent to Tumors by Using Focused Ultrasound: Study in a Murine Model," Radiology, 234(2): 431-437, 2005.
Zerhouni et al., "Human Heart: Tagging with MR imaging—a method for noninvasive assessment of myocardial motion," Radiology 169(1): 59-63, Oct. 1988.
Zheng et al., "Ultrasonic measurement of depth-dependent transient behaviors of articular cartilage under compression," *Journal of Biomechanics*, 38:1830-1837 (2005).
Zheng et al., "High Resolution ultrasound elastomicroscopy imaging of soft tissues: system development and feasibility," *Physics in Medicine and Biology*, vol. 49, No. 17, pp. 3925-3938 (Sep. 7, 2004).
Zwanenburg et al., (2004) "Timing of cardiac contraction in humans mapped by high-temporal-resolution MRI tagging: early onset and late peak of shortening in lateral wall," Am J Physiol Heart Circ Physiol 286:H1872-1880.
Chang et al., "3-D US Frame Positioning Using Speckle Decorrelation and Image Registration," *Ultrasound in Medicine & Biology*, Jun. 2003, 29(6): pp. 801-812.
Achilli, Luca G.C., Abstract for "Physically Crosslinked Chitosan Based Hydrogels for Biomedical Applications," PhD Thesis, University of London, 2008.
Cavalieri et al., "Stable Polymeric Microballoons as Multifunctional Device for Biomedical Uses: Synthesis and Characterization," *Langmuir*, 2005, 21(19): pp. 8758-8764.
Chappell et al., "Targeted Delivery of Nanoparticles Bearing Fibroblast Growth Factor-2 by Ultrasonic Microbubble Destruction for Therapeutic Arteriogenesis," *Small*, Oct. 2008, 4(10): pp. 1769-1777.
Demarteau et al., "Dynamic Compression of Cartilage Constructs Engineered from Expanded Human Articular Chondrocytes," *Biochemical and Biophysical Research Communications*, 2003, 310: pp. 580-588.
Nair, Ashwin M., "Novel Preparation of Polymeric Scaffolds for Tissue Engineering Using Phase Separation With Protein Microbubble Incorporation," PhD Thesis, University of Texas at Arlington, 2006.
Nair et al., "A Novel Preparation of Degradable Scaffolds Using BSA Microbubbles as Porogen," *Engineering in Medicine and Biology Workshop*, IEEE Dallas, 2007, pp. 31-34.
Nair et al., "Novel Polymeric Scaffolds Using Protein Microbubbles as Porogen and Growth Factor Carriers," *Tissue engineering: Part C—Methods*, Feb. 2010, 16(1): pp. 23-32.
Terraciano et al., "Differential Response of Adult and Embryonic Mesenchymal Progenitor Cells to Mechanical Compression in Hydrogels," *Stem Cells*, 2007, 25:pp. 2730-2738.

\* cited by examiner

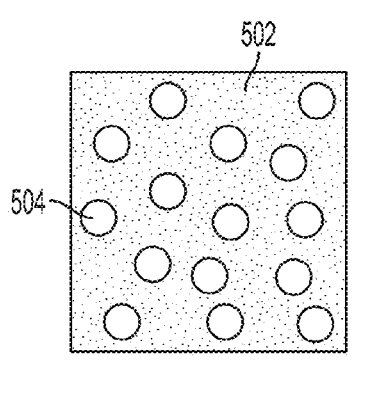
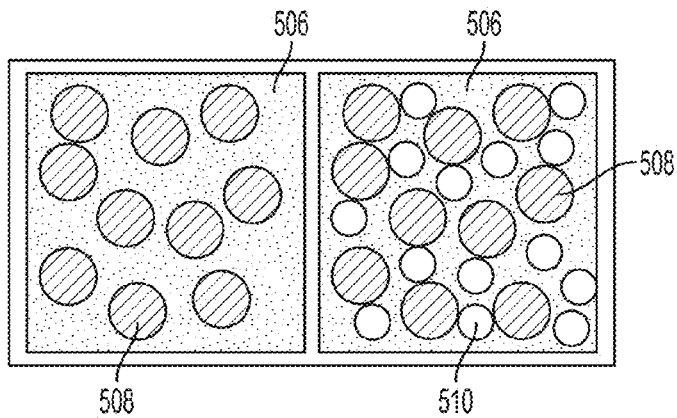
FIG. 5A    FIG. 5B
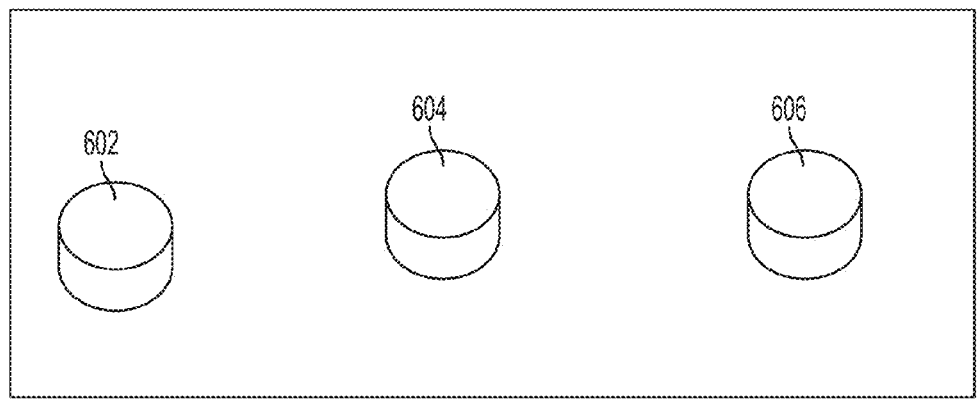
FIG. 6

MICROBUBBLE DEVICES, METHODS AND SYSTEMS

CROSS-REFERENCE TO RELATED APPLICATIONS

This application is a divisional of U.S. application Ser. No. 13/393,273, filed Apr. 30, 2012, which is a U.S. national stage entry of International Application No. PCT/US10/47263, filed Aug. 31, 2010, which claims the benefit of U.S. Provisional Application No. 61/239,000, filed Sep. 1, 2009, and U.S. Provisional Application No. 61/304,782, filed Feb. 15, 2010, all of which are incorporated by reference herein in their entireties.

STATEMENT REGARDING FEDERALLY SPONSORED RESEARCH

This invention was made with government support under AR046568 awarded by the National Institutes of Health (NIH). The government has certain rights in the invention.

SUMMARY

Damage to articular cartilage is a common condition affecting the joints of millions of people. This is a major problem considering the poor regenerative capacity of adult articular cartilage and the disability and pain that accompanies these injuries. An estimated 27 million Americans age 25 and older have osteoarthritis (OA). The total direct cost of OA is estimated at $28.6 billion dollars a year in related medical costs. More than 680,000 arthroplastic procedures are performed each year in the U.S.

Tissue engineering strategies promise improvements in health care for conditions such as damaged cartilage. Effective treatment of cartilage injuries using tissue engineering strategies may prevent the development of OA and may reduce the need for a total joint replacement. While tissue engineering strategies hold promise for new treatment options, challenges remain.

For example, the ability to supply nutrients to cells is a useful feature of engineered tissues but an overly porous scaffold can result in cell product loss to the culture medium rather than its retention. An insufficiently porous scaffold or medium can lead to nutrient deficiencies for cells at the construct core region (e.g., regions remote from perfused surfaces). Striking a balance between these factors is challenging as construct dimensions increase or as cells deposit matrix with time in culture. A preferred scaffold has a global architecture that uniformly distributes nutrients throughout while maintaining an optimal local pore-structure around cells.

Hydrogels may provide three-dimensional scaffolds for cartilage basic science and tissue engineering applications due to their inherent similarities to native cartilage, including high water content, ability to maintain the chondrocyte phenotype as well as ease of uniform cell seeding. Hydrogel crosslinking density defines the local pore size around encapsulated cells responsible for entrapment of cell-synthesized molecules that form extracellular matrix (ECM) tissue. If porosity is too high, cell products are released into the bathing culture media, whereas if the porosity is too low, cells become nutrient limited.

Embodiments of the present invention were conceived in light of the above mentioned tissue engineering challenges, among other things.

In an embodiment, microbubbles are used to modify the properties of a clinically-relevant hydrogel scaffold for applications such as cartilage tissue engineering. Microbubble-dispersed hydrogel constructs may be characterized in terms of their physical properties (e.g., mechanical properties, diffusivity) with culture time; as well as their biocompatibility in culture.

An embodiment includes the application of microbubble technology as a means of fabricating cell seeded hydrogel scaffold constructs that retain an optimal polymer crosslinking density for extracellular matrix production/retention while providing a uniform macro-porosity that increases the effective diffusivity of soluble factors into cell-seeded scaffolds may provide benefits as discussed herein. Strategies may include triggering the dissolution of microbubbles, permitting them to become fluid-filled, and acting as macro-pores thereby reducing path length an increasing nutrient transport and signaling.

In another embodiment, a method of altering the physical properties of a clinically-relevant hydrogel scaffold includes incorporating gas-filled microbubbles into the hydrogel scaffold, whereby the physical properties are altered such that the effective diffusivity of nutrients is increased. An exemplary method further includes mixing gas-filled microbubbles with molten agarose solutions at concentrations ranging from $1 \times 10^8$ to $1 \times 10^9$ microbubbles per milliliter (μb/mL); and allowing the solution to cool so that the gel solidifies with the bubbles contained inside. This method allows the size and concentration of the bubbles to be carefully controlled and further allows for a very uniform distribution of bubbles to be maintained. Additionally, this method yields no cell toxicity resulting from the formulation process.

BRIEF DESCRIPTION OF THE DRAWINGS

FIGS. 5A-5B are schematic depictions of microbubble design and characterization in two studies.

FIG. 6 is a series of acellular agarose discs with varying concentrations of microbubbles. Freshly cast acellular agarose discs with varying concentrations of microbubbles are depicted. From left to right, ctrl (no bubbles), $1.5 \times 10^8$, and $3 \times 10^8$ bubbles/mL.

DETAILED DESCRIPTION

Figure 1:
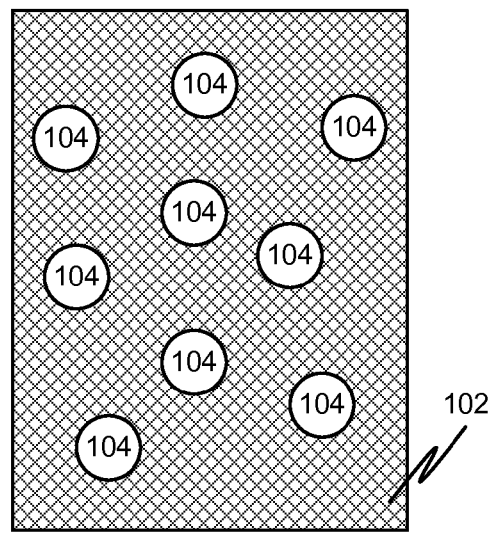
FIG. 1 is a diagram of a hydrogel scaffold with dispersed microbubbles in accordance with the present disclosure.

FIG. 1 is a diagram of a hydrogel scaffold 102 with dispersed microbubbles 104 in accordance with the present disclosure. The hydrogel 102 may be a tissue engineering scaffold. A tissue engineering scaffold may provide nutrient exchange to cells embedded therein. This is particularly advantageous in scaffolds of relatively greater thickness. The tissue engineering scaffolds further provides for cellular division and expansion in a three-dimensional matrix wherein the third dimension (i.e., thickness) is substantially proportionate to the other dimensions. Additionally, the tissue engineering scaffold may be used to achieve native tissue properties in relatively small samples.

Microbubbles may be formulated by emulsifying a lipid formulation with a hydrophobic gas, sulfur hexafluoride ($SF_6$) or perfluorobutane (PFB). The lipid formulation consists of lipid molar ratios of 90% 1,2-distearoyl-sn-glycero-3-phosphocholine (DSPC) and 10% Polyethylene Glycol (40) Stearate (PEG-40). The microbubbles may be formulated with other emulsifying agents as well, including but not limited to, 1,2-dimyristoyl-sn-glycero-3-phosphoethanolamine-N-[methoxy(polyethylene glycol)-2000] (DSPE-PEG2K), 1,2-dimyristoyl-sn-glycero-3-phosphoethanolamine-N-[methoxy(polyethylene glycol)-5000] (DSPE-PEG5K), and other DSPE-PEG variants.

Figure 2:
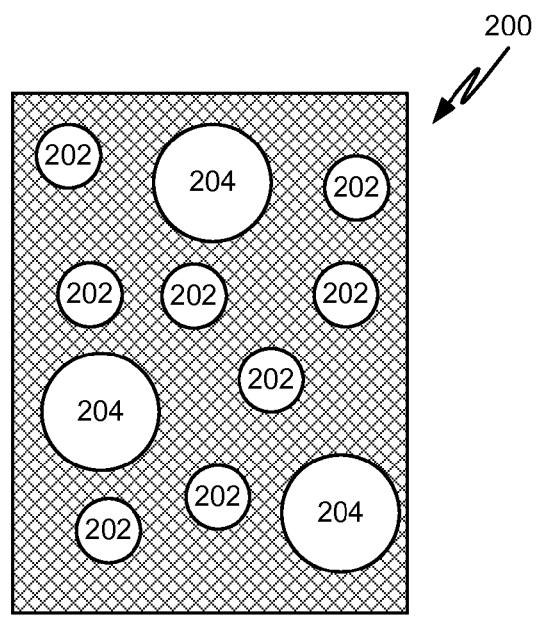
FIG. 2 is a diagram of a hydrogel scaffold with dispersed microbubbles and cells in accordance with the present disclosure.

FIG. 2 is a diagram of a hydrogel tissue engineering scaffold 200 having dispersed microbubbles 202 and cells 204. The cells 204 may be chondrocyte cells, or any other type of cell suitable for tissue engineering.

Figure 3:
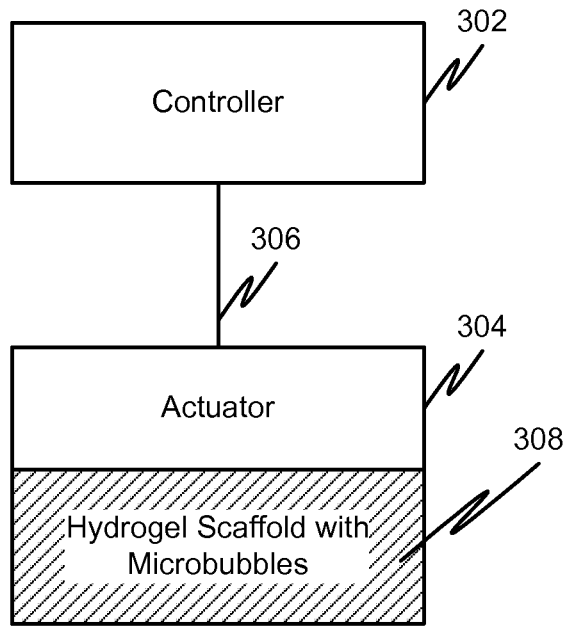
FIG. 3 is an automatic tissue culture system in accordance with the present disclosure.

FIG. 3 is a system for dynamic deformational loading of a hydrogel tissue engineering scaffold adapted to culture cells. In particular, a system 300 includes a processor 302 and an actuator 304 coupled to the processor 302 via a link 306. The actuator 304 is disposed adjacent to a hydrogel scaffold 308.

In operation, the processor 302 is programmed to activate the actuator 304 according to a predetermined timing. For example, the processor 302 may apply dynamic deformational loading at one or more predetermined times during a cell culture cycle. The system may continue to further culture the cells after the one or more applications of dynamic deformational loading. The dynamic deformational loading may have an amplitude that destroys some or all of the microbubbles and releases gas from microbubbles within the hydrogel and allows liquids (e.g., nutrients) to fill the spaces previously occupied by the microbubbles. The loading may have an amplitude that places a load on the hydrogel, but does not destroy all, or a significant portion, of the microbubbles.

Figure 4:
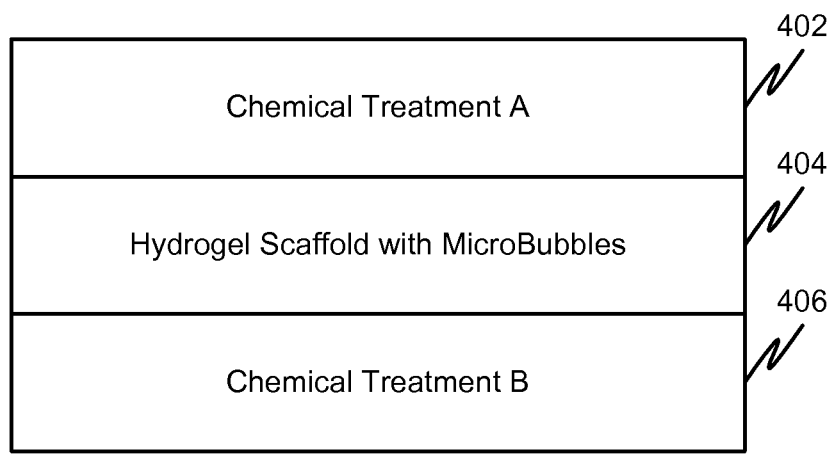
FIG. 4 is a diagram of a hydrogel scaffold with two chemical treatments in accordance with the present disclosure.

FIG. 4 is a cell culture system 400 in which a first chemical treatment 402 is applied to a top surface of a hydrogel scaffold 404. A second chemical treatment 406 is applied to a bottom surface of the hydrogel scaffold 404. The first chemical treatment 402 and the second chemical treatment 406 can be the same or different. The hydrogel scaffold 404 may have gas-filled microbubbles incorporated such that the hydrogel scaffold 404 floats above the second chemical treatment 406 and below the first chemical treatment 402.

The present inventors conducted two studies, Study A and Study B, to characterize microbubble-dispersed hydrogel constructs in terms of their (1) physical properties (e.g., mechanical properties, diffusivity) with culture time; as well as their (2) biocompatibility in culture. See, for example, Study A and Study B, shown in FIGS. 5A-5B.

As part of Study A, microbubbles 504 were created through sonication of distearoyl-phosphatidylcholine (DSPC) lipid with perfluorobutane (PFB) gas. The bubbles in the resulting mixture were counted and sized (~0.5-10 µm) and combined with agarose 502 to create acellular discs of three concentrations. FIG. 6 shows freshly cast acellular agarose 602, 604, and 606 with microbubble concentrations of 0, 1.5, and $3 \times 10^8$ bubbles/mL. The discs were maintained in PBS at 37° in an incubator for 28 days and examined for changes in mechanical properties, changes in bubble density, and changes in diffusivity. Microscope testing with digital image correlation was used to evaluate changes in mechanical properties. Changes in diffusivity were tested for using fluorescently tagged 70 kDa dextran.

Figure 7A:
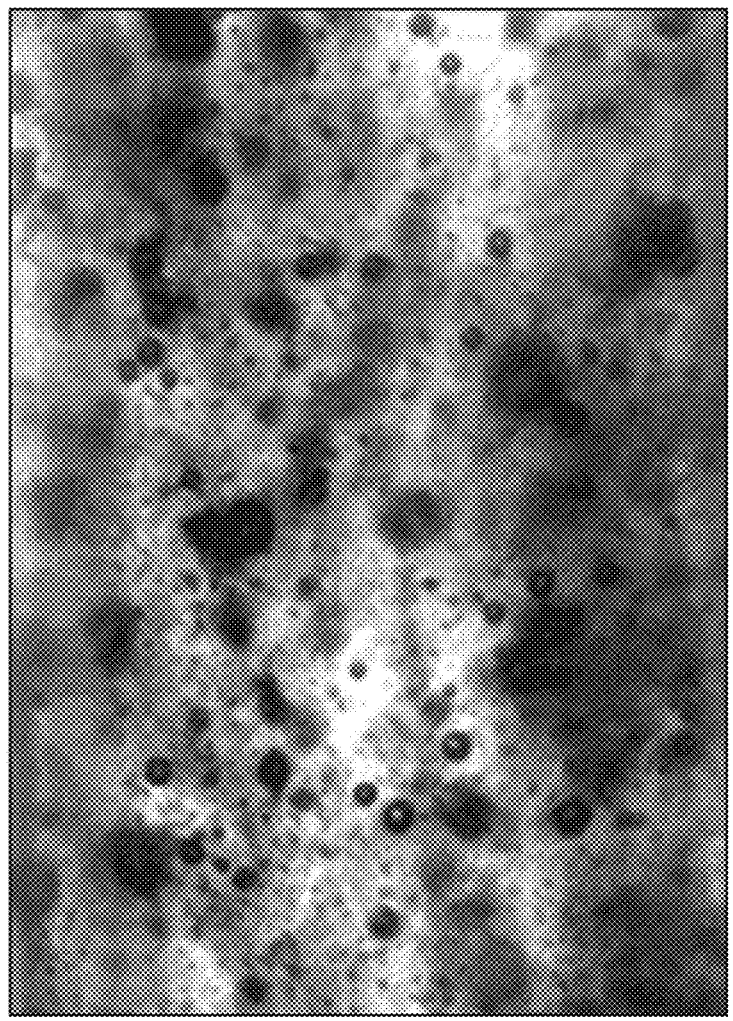
FIG. 7A is a cross-sectional image showing microbubble concentration in a construct on day 0 of a cell culture cycle. Depicted is a cross-sectional image showing bubbles (black dots) on Day 0 of 7-day culture period (bar=20 μm).
Figure 7B:
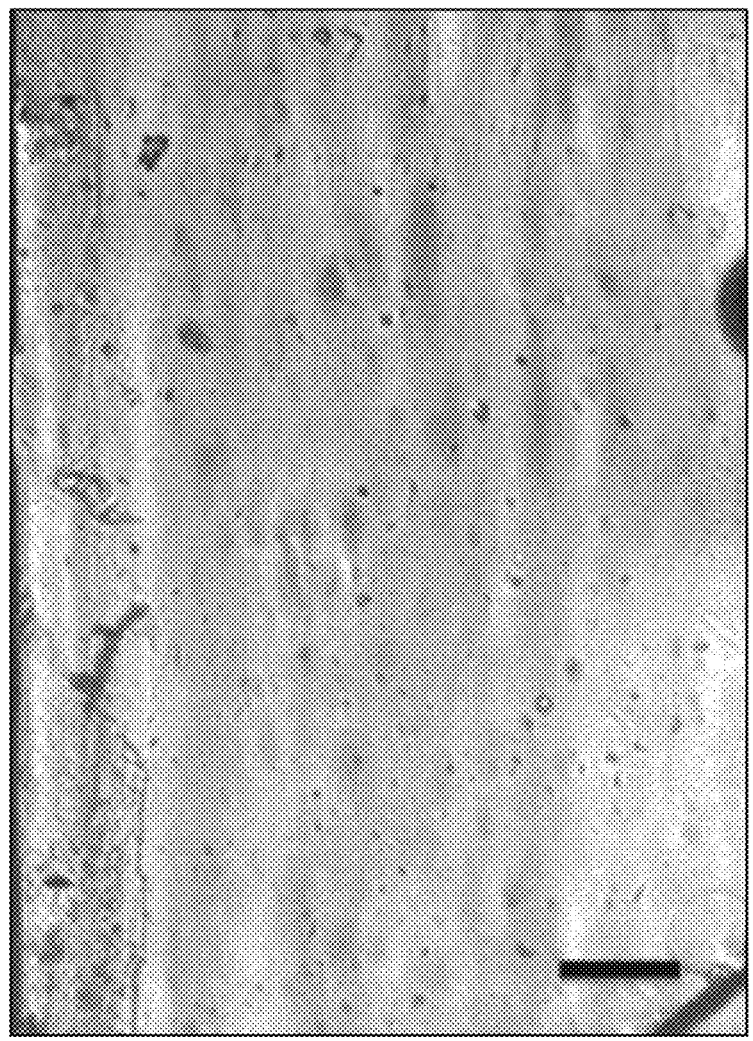
FIG. 7B is a cross-sectional image showing microbubble concentration in a construct on day 7 of a cell culture cycle. Depicted is a cross-sectional image showing loss of bubbles (black dots) over 7-day culture period (bar=20 μm).
Figure 7C:
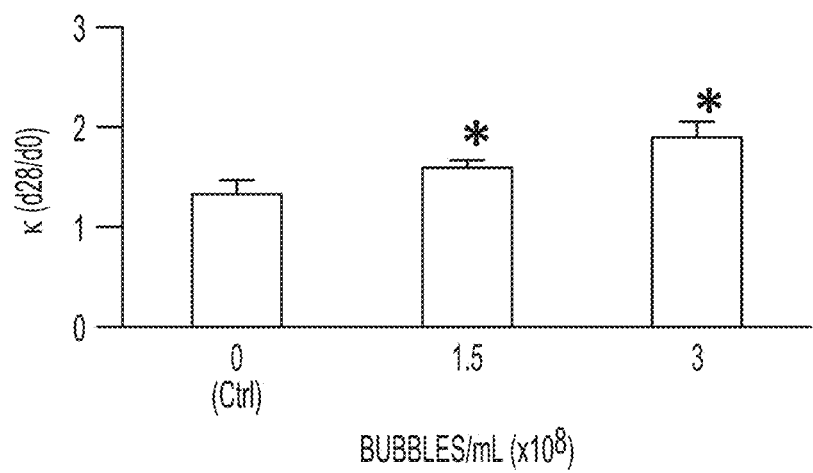
FIG. 7C is a graph of effective diffusivity in constructs of varying microbubble concentration. Normalized partition coefficient (κ) of 70 kDa dextran (day 28 normalized to day 0 values), *$p<0.01$ against all other groups.
Figure 8A:
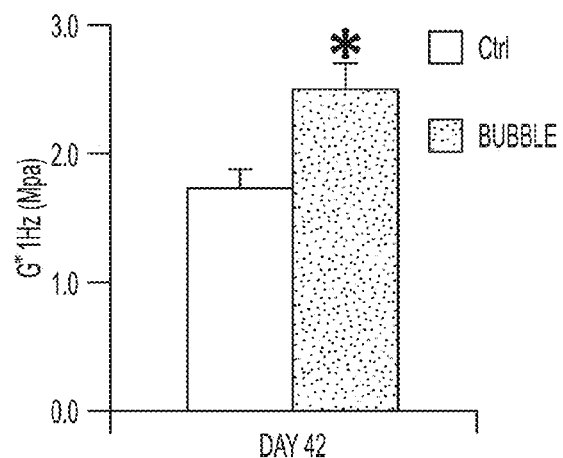
FIG. 8A is a graph of a dynamic modulus in constructs of varying microbubble concentration. Dynamic Modulus on day 42 chondrocyte-seeded discs w/wo bubbles, *p<0.01.
Figure 8B:
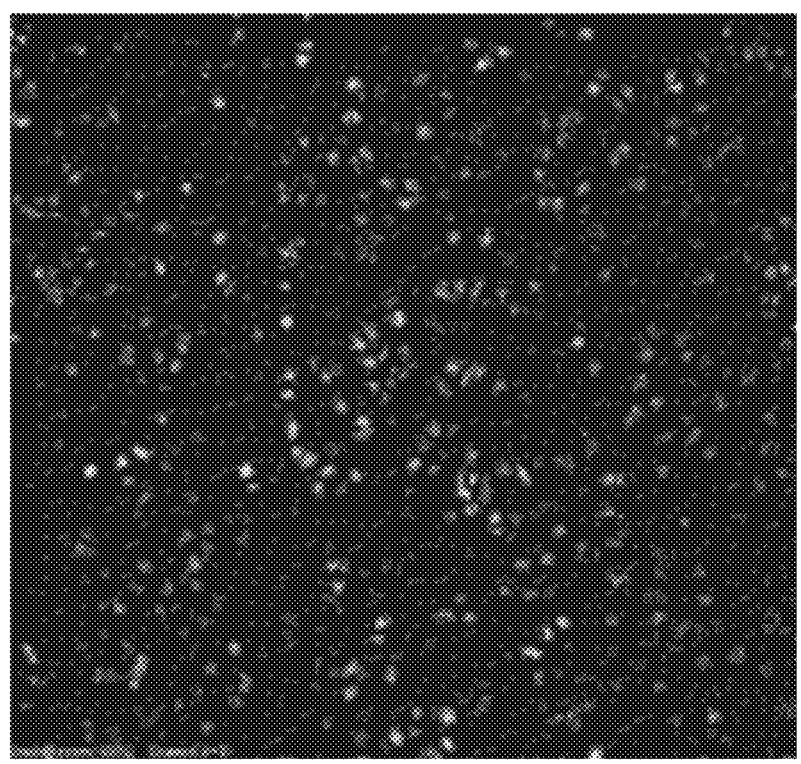
FIG. 8B shows a Live/Dead image on day 42 (bar=100 µm).

By day 7, bubbles were no longer visible under the microscope, whereas they were highly visible on initial casting. See, for example, FIGS. 8A and 8B. Higher concentrations of bubbles created higher opacity in constructs, as shown in FIG. 7, and decreased Young's modulus. For example the control construct exhibited a Young's modulus of 11.31±2.2 kPa, the construct having a microbubble (µb)

concentration of $1.5 \times 10^8$ bubbles/mL showed a Young's modulus of $9.3 \pm 1.1$ kPa, and the construct having a μb concentration of $3.0 \times 10^8$ bubbles/mL showed a Young's modulus of $7.75 \pm 1.4$ kPa. Local mechanical measurements performed using digital image correlation and a custom microscopy-based material testing device indicated a uniform strain field across the constructs with and without microbubbles throughout the study (not shown). By day 28, the effective diffusivity of 70 kDa dextran increased significantly over day 0 values and over day 28 controls. See, for example, FIG. 8.

Study B included an initial biocompatibility study; microbubbles 510 were created by vigorous shaking of DSPC lipid in the presence of PFB gas using a dental amalgamator. The resulting bubble mixture was combined with primary chondrocytes 508 ($30 \times 10^6$ cells/mL) isolated from fresh bovine wrist joints and suspended in molten agarose 506 (Type VII, Sigma). Cylindrical discs (Ø4×2.3 mm) were cast and cultured for 42 days in chemically-defined Dulbecco's Modified Eagle Medium (DMEM) according to an optimized protocol. Constructs were examined for changes in mechanical and biochemical properties and cell viability. Changes in mechanical properties were evaluated based on, for example, Young's modulus and dynamic modulus at 1 Hz using a custom material testing device. Changes in biochemical properties were evaluated based on, for example, glycosaminoglycans (GAG) using the 1,9-dimethylmethylene blue (DMMB) assay Cell viability was evaluated using live/dead staining.

Cells in the bubble group remained viable throughout the 42-day study and developed, for example, a higher dynamic modulus than the control (bubble free) group, as shown in FIG. 4. There were no apparent differences in Young's modulus, GAG (e.g., bubble=$10.8 \pm 1.2\%$ ww, Control=$9.5 \pm 1.4\%$ ww) or collagen content (e.g., bubble=$2.1 \pm 0.5\%$ ww, Control=$2.0 \pm 0.4\%$ ww).

As can be readily seen from Study A and Study B, for example, microbubble incorporation may result in changes to hydrogel scaffold physical properties. The candidate hydrogel of study was clinically-relevant agarose, but other hydrogel materials (e.g., alginate, PEG) may be used. The ability to combine microbubbles and cells into the molten hydrogel before gel polymerization permits hydrogel constructs to be fabricated without modifying standard protocols. Moreover, this ability retains the advantage of uniform cell seeding typically associated with hydrogel scaffolds. This is more challenging to achieve for pre-fabricated fibrous or porous scaffolds that require a secondary cell seeding step.

Providing adequate nutrient access to cells becomes increasingly difficult with engineered constructs of increasing dimensions. Culturing anatomically-shaped constructs, for example, pose a significant challenge due to nutrient limitations at the heart of these large constructs. The diffusivity measurement presented here suggests that incorporation of dispersed microbubbles in agarose increases access of nutrients. See, for example, Study A. These results may help explain the enhanced tissue properties observed in the cellular study. See, for example, Study B. Future studies will be performed to identify the specific mechanisms mediating the enhanced tissue development associated with microbubble incorporation into the hydrogel scaffolds.

Under culture conditions, the encapsulated bubbles dissolved within a week. The transitory nature of the bubbles may serve to leave behind pores that alter the structure and properties of the scaffold. These pores, in turn, may fill with the surrounding nutrient medium. Bubble properties may be modulated to extend the stability of the bubbles in culture as well as incorporation of growth factors to their surfaces. In addition to their other uses, microbubbles may have potential for applications in regenerative medicine strategies for cartilage repair. Other potential applications include, for example: (1) the application of dynamic hydrostatic loading of hydrogels with microbubbles. This could provide a physical stimulus (akin to dynamic deformational loading) that would take advantage of the compressibility of air over water; (2) The use of microbubbles to incorporate growth factors into a hydrogel; and (3) Applying different chemical stimulus above and below the floating constructs to take advantage of the fact that microbubble-laden hydrogels float.

The ability to supply nutrients to cells is a useful feature of engineered tissues but an overly porous scaffold can result in cell product loss to the culture medium rather than its retention. An insufficiently porous scaffold or medium can lead to nutrient deficiencies for cells at the construct core region (e.g., regions remote from perfused surfaces). Striking a balance is challenging as construct dimensions increase or as cells deposit matrix with time in culture. A preferred scaffold has a global architecture that uniformly distributes nutrients throughout while maintaining an optimal local pore-structure around cells.

Hydrogels have been adopted for cartilage basic science and tissue engineering due to their high water content, ability to maintain the chondrocyte phenotype as well as ease of uniform cell seeding. An optimized media formulation may be combined with the application of dynamic deformational loading to cell-seeded hydrogel constructs to promote the development of engineered cartilage with native tissue mechanical properties via physical cues to cells as well as enhanced solute transport.

Microbubble technology may provide means for fabricating cell seeded hydrogel scaffold constructs that retain an optimal polymer crosslinking density for extracellular matrix (ECM) production while providing a uniform macro-porosity that increases the effective diffusivity of soluble factors into cell-seeded scaffolds. In the disclosed approach, a suspension of microbubbles and cells are mixed with unpolymerized hydrogel and then permitted to gel (see FIG. 14). A solution of microbubbles (μb) 1402 and a solution of chondrocytes (cell) 1404 are combined 1406 and mixed with an equal volume of 4% agarose hydrogel 1406 to fabricate chondroycte-seeded, microbubble infused agarose constructs 1410. Control chondrocyte-seeded agarose constructs 1412 can be fabricated by combining equal volumes of 1404 and 1406. Microbubble dissolution in constructs can be triggered using hydrostatic pressure 1414, creating fluid-filled macro-pores 1416, and constructs cultured under free-swelling 1418 or dynamic deformational loading 1420 conditions for up to 56 days.

Figure 9A:
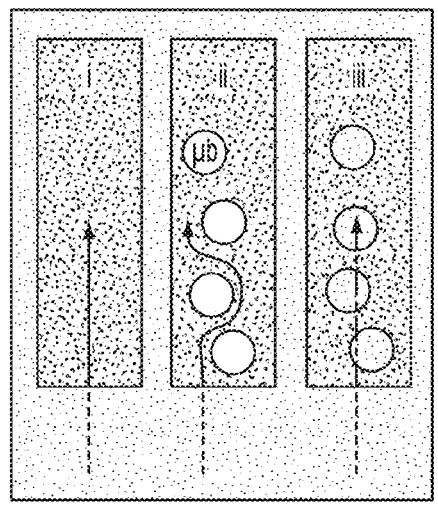
FIG. 9A shows a schematic of solute diffusion paths in (i) hydrogel; (ii) hydrogel with gas microbubbles (µb); and (iii) fluid-filled pores after µb dissolution.
Figure 9B:
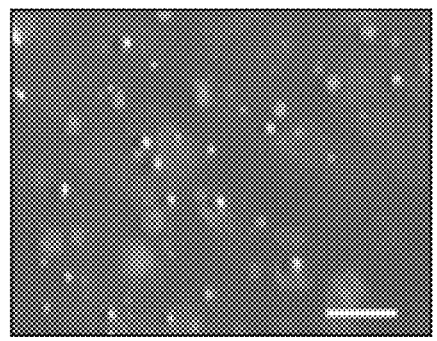
FIG. 9B shows microbubbles suspended in hydrogel.
Figure 9C:
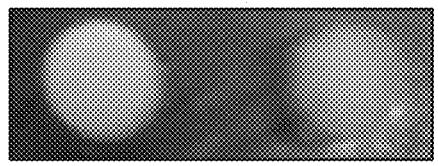
FIG. 9C shows microbubble infused hydrogel construct pre/post partial microbubble dissolution was triggered (becoming less opaque).
Figure 16A:
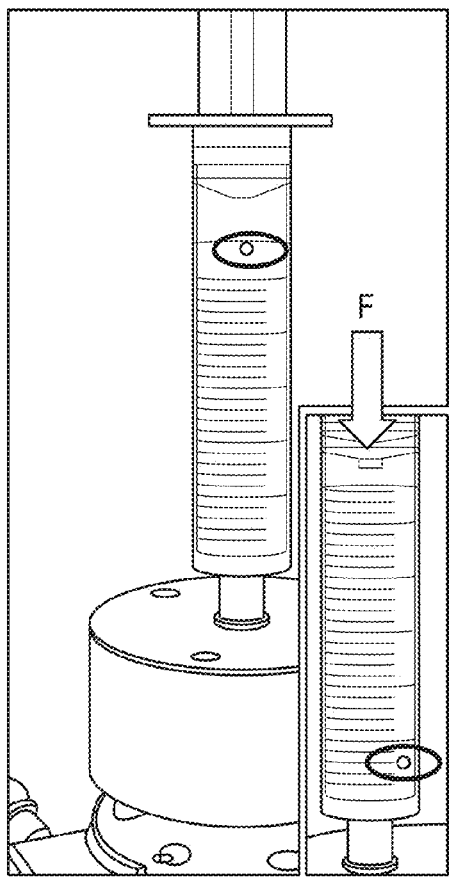
FIGS. 16A-16B shows gas-filled microbubble (noted by red ellipse) in hydrogel constructs subjected to hydrostatic pressure and becoming fluid-filled.
Figure 16B:
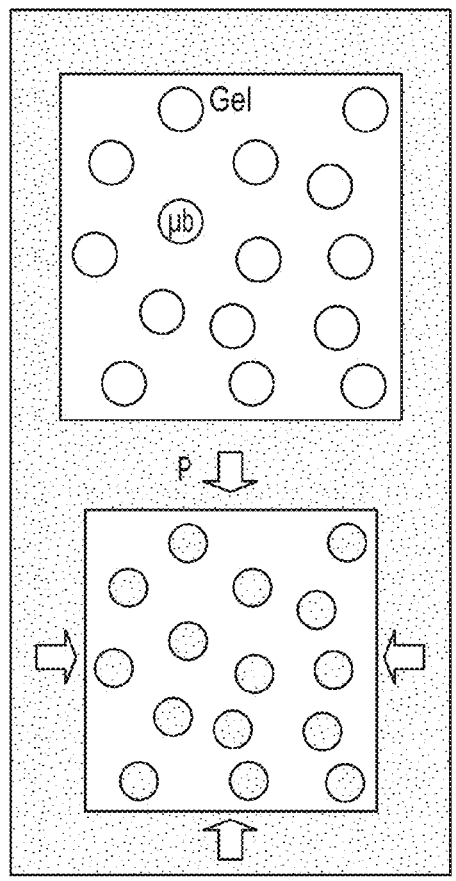
Figure 17A:
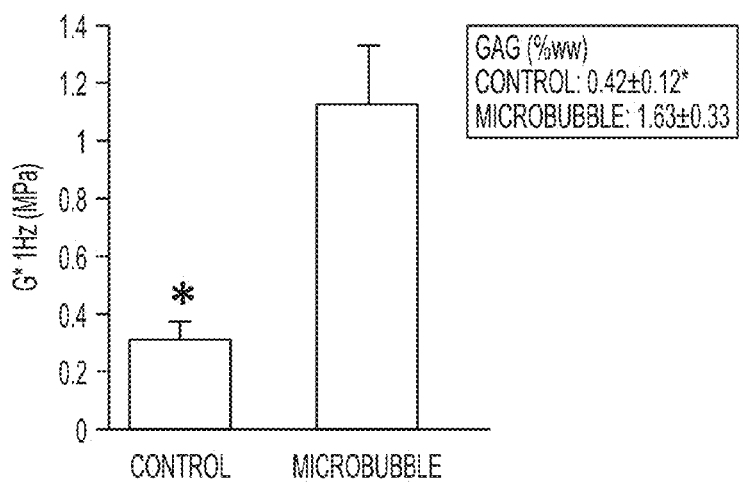
FIGS. 17A-17C show dynamic modulus (G*), vital staining and safranin-O staining for GAG of chondrocyte-seeded agarose constructs infused with microbubbles and cultured for 28 days. Control: 2% agarose construct without bubbles.
Figure 17B:
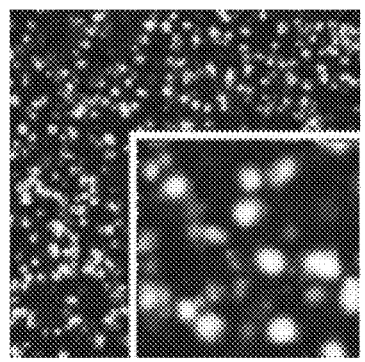
Figure 17C:
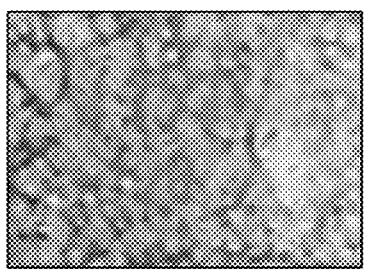

When the dissolution of the biocompatible gas is triggered, the microbubbles become fluid-filled, (FIGS. 16A-16B). At this time, fluid-filled pores act to bridge regions of cell seeded cross-linked hydrogel, decreasing the effective nutrient path length (FIG. 9A) and increasing solute diffusivity. This effect has been confirmed as indicated in laboratory data shown in FIGS. 15A-16B. The effect leads to increased tissue properties relative to microbubble-free control gels (FIGS. 17A-17C). Microbubble infused hydrogel scaffolds may exhibit increasing solute diffusivity in a microbubble dose-dependent manner.

Experiments have established that a tissue construct fabricated from chondrocyte-seeded hydrogel constructs with initial microbubble concentrations yielded 25%, 50%, and 100% greater diffusivity of fluorescently labeled dextran (70 kDa) than the hydrogel without microbubbles. Chondrocyte-seeded, hydrogel scaffolds incorporated with microbubbles may yield engineered tissues with properties closer to the native tissue compared to the same scaffolds without microbubbles. The properties of constructs with microbubbles may be dependent on timing of microbubble dissolution. Application of applied dynamic deformational loading may enhance the beneficial effects of microbubble infused hydrogels. Using predefined microbubble conditions, constructs may be cultured for predefined intervals (e.g., 56 days) and dissolution of gas-filled microbubbles triggered at one or more specific times along the time line. For example, they may be triggered on day 0 or day 14 of a 56 day interval.

Gas filled microbubbles may provide hydrogel scaffold that can be compressed, for example, isotropically. Such a deformation capability may be provided to create a corresponding type of mechanical stimulation to promote cell growth. In embodiments, the susceptibility to be isotropic compression may be modified by selective dissolution of microbubbles.

Cell access to fluid-filled macro-pores may be used to decrease nutrient path length and provide additional space for tissue elaboration at culture points when tissue is denser. Their benefit may be of greatest significance to continued functional tissue development (see FIG. 12).

Figure 10:
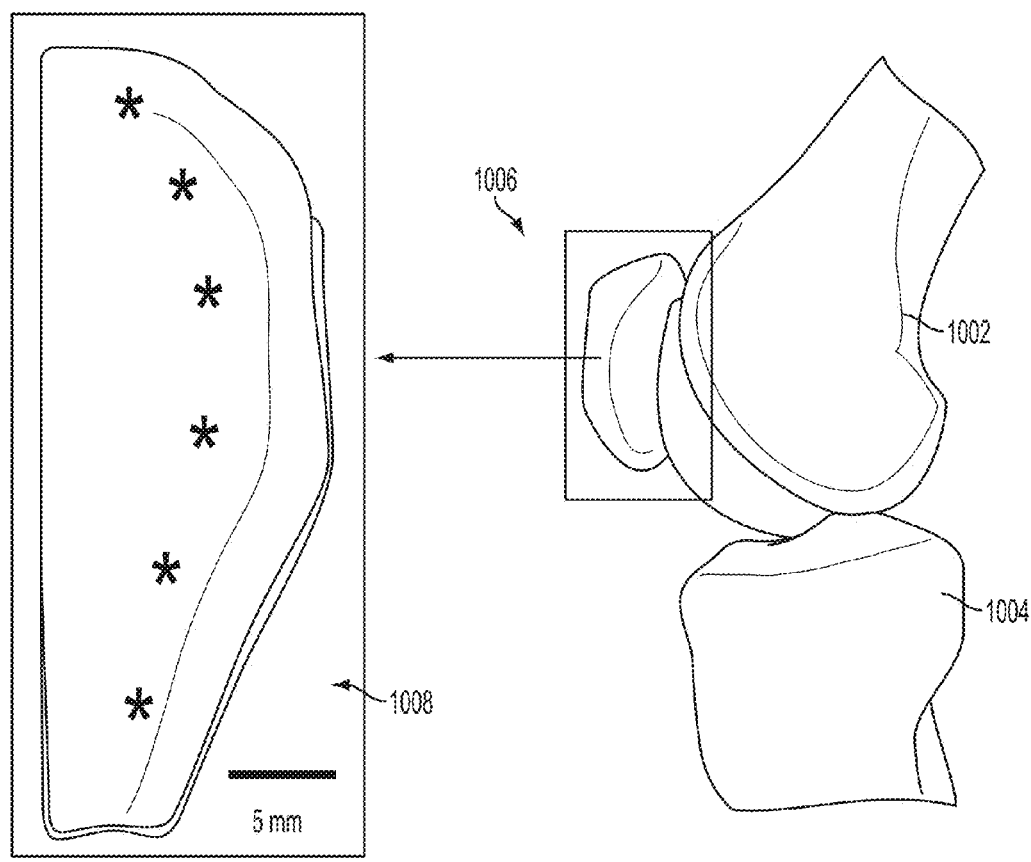
FIG. 10 shows an engineered knee cap (patella) construct with proteoglycan-rich matrix (red safranin-O stain) limited to gel periphery indicating diffusion limitations, where * interface between gel-bony substrate.

The scaling of engineered tissues aimed at repair of focal cartilage defects to much larger articular constructs indicated for repair/replacement of joints (e.g., joint 1006 connecting bones 1002 and 1004) suffering from severe trauma and degenerative joint disease may require the fabrication of tissues (e.g., patella construct 1008) with native mechanical properties which are reliant in part on the ability to provide sufficient nutrients to cells residing in the growing tissue, see FIG. 10. The relatively low tissue properties achieved reflect the development of inhomogeneous tissue properties through the engineered construct thickness that develop with culture time. It has been observed that constructs of greater than 1 mm thickness develop a "u-shaped" axial distribution of properties with central regions having less matrix elaboration relative to stiffer peripheral regions.

In embodiments, the composition of a microbubble is a gas core stabilized by a shell comprised of proteins, lipids or polymers. The macro-porosity of bioscaffolds is typically formed using sacrificial porogens that are dissolved away, leaving behind their vacated space. Lyophilization of hydrogels (such as for hyaluronan and collagen) can result in sponge-like scaffolds with macro-porosity. For these systems, cells are introduced via various seeding techniques that depend on the effectiveness of cell infiltration to central regions of the construct to achieve uniform seeding. Unlike hydrogels, pore sizes in these constructs are constrained to a minimum diameter that allows for cell infiltration.

Figure 12:
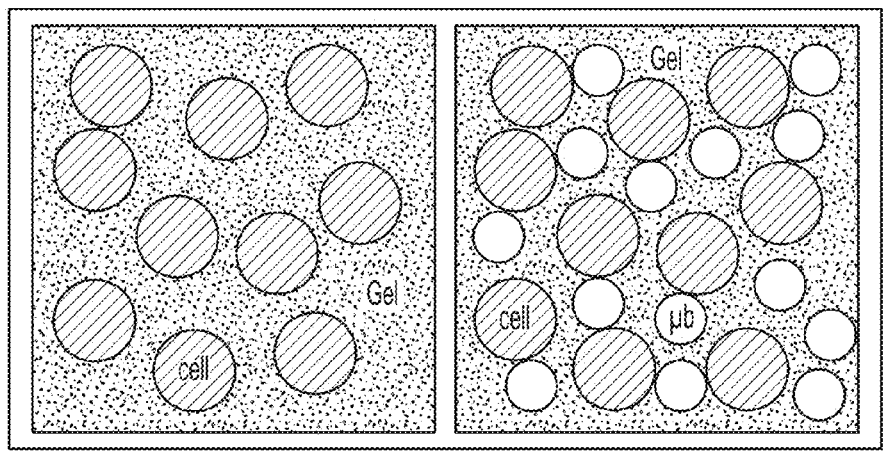
FIG. 12 is a schematic of hydrogel conditions relevant to the disclosed subject matter illustrating cellular constructs with and without microbubbles.
Figure 14:
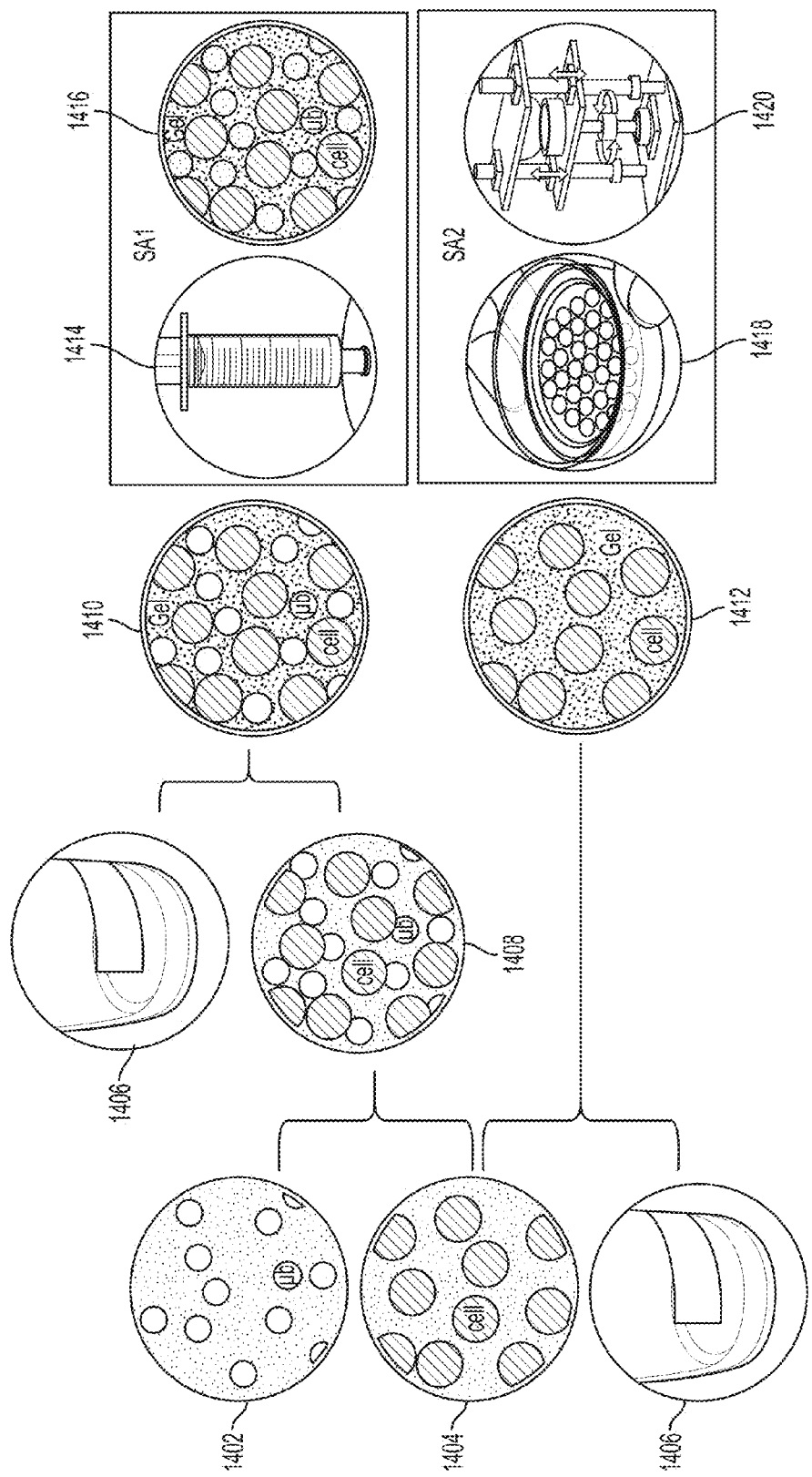
FIG. 14 illustrates a procedure according to embodiments of the disclosed subject matter.
Figure 15A:
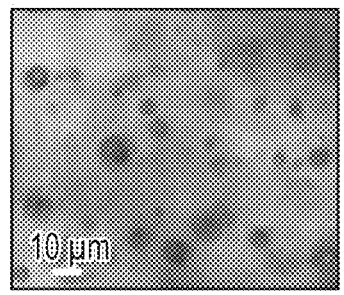
FIGS. 15A-15C show microbubbles in solution, acellular hydrogel constructs with increasing microbubble volume fraction and properties of microbubble infused acellular hydrogels. *p<0.05 vs. control (0%).
Figure 15B:
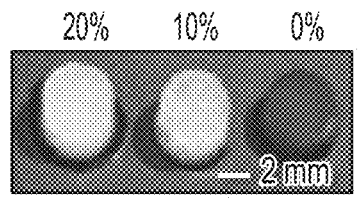
Figure 15C:
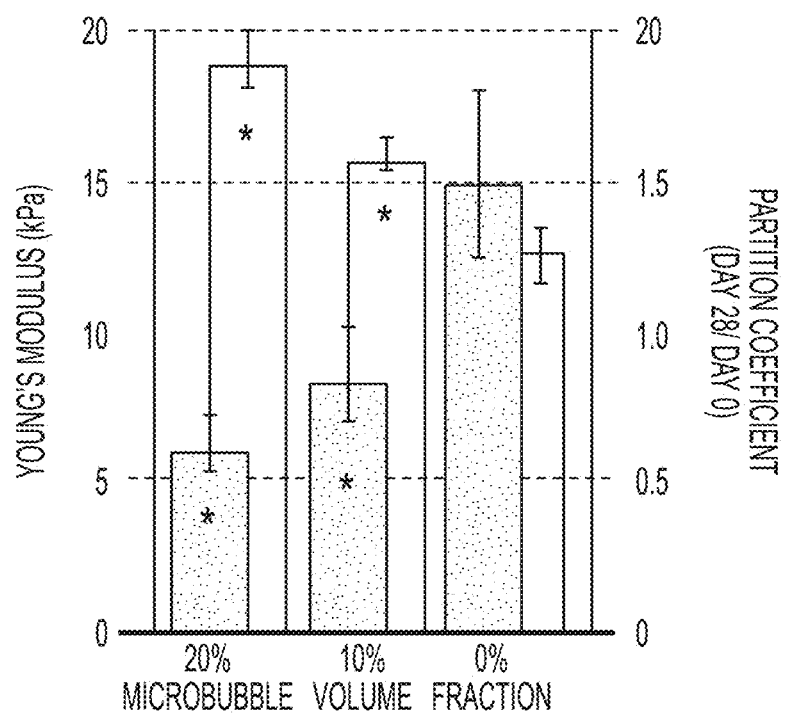

A strategy to introduce macro-porosity to hydrogels in their hydrated form typically adopted for biological applications may include the mixing of unpolymerized hydrogel (liquid) with cells and gas-filled microbubbles followed by activation of hydrogel polymerization, resulting in a suspension of cells and microbubbles in a (solid) cross-linked hydrogel (FIGS. 12, 14). To create macro-porosity, the gas-filled microbubbles may be triggered to dissolve (such as by application of hydrostatic pressurization, Section P2-FIG. 16B), releasing their biocompatible gas, and vacating a pore space that is immediately filled with culture media.

As microbubble dissolution can be controlled, cell access to fluid-filled macro-pores can be timed so as to decrease nutrient path length and provide additional space for tissue elaboration at later culture points when tissue is denser and their benefit may be of greatest significance to continued functional tissue development (see FIGS. 9A-9C and 13).

Figure 11A:
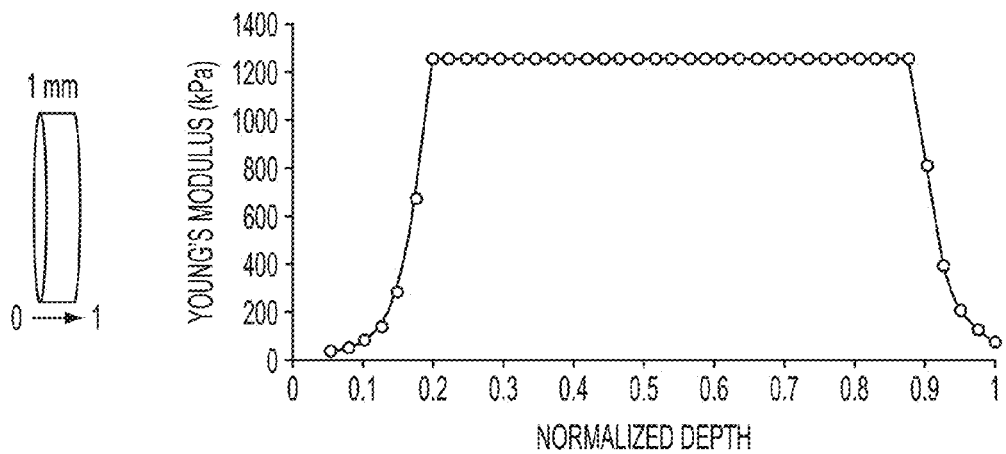
FIGS. 11A and 11B show differences in properties for varying construct thicknesses. Nutrient limitations lead to lower tissue mechanical properties for chondrocyte-seeded agarose constructs due to development of axial inhomogeneity (2 mm thick). More uniform properties, and overall higher modulus, are achieved in a 1 mm thick construct. Serum-free media.
Figure 11B:
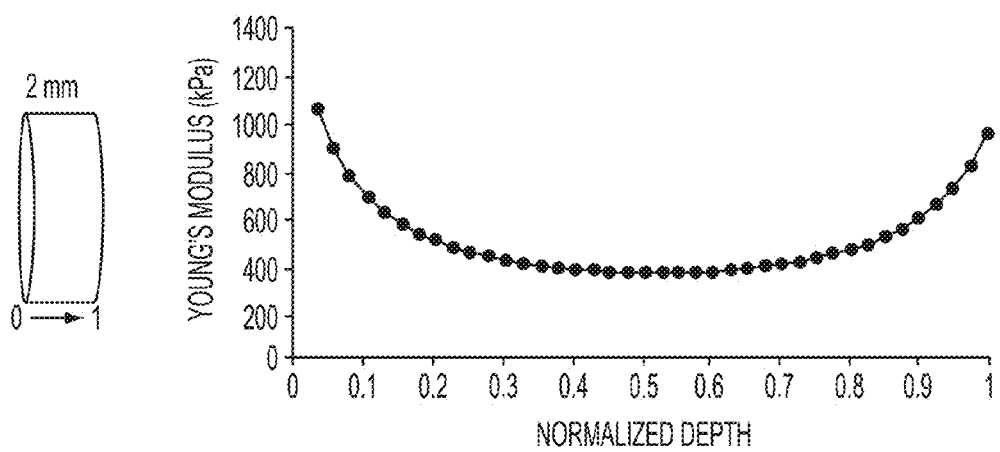
Figure 13:
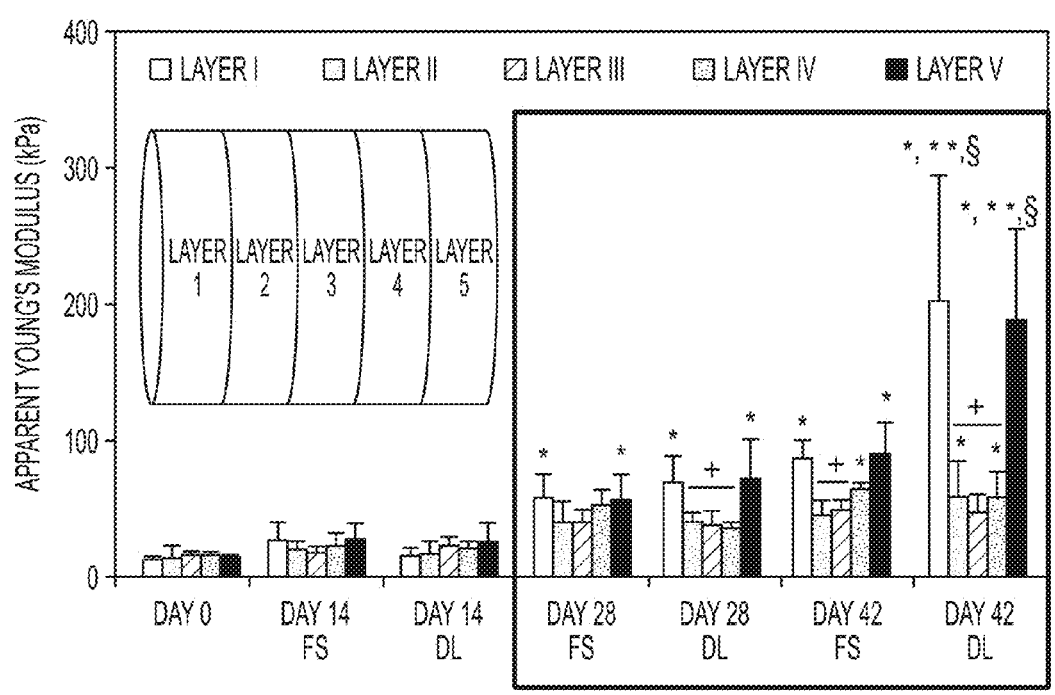
FIG. 13 is a graph illustrating chondrocyte-seeded agarose hydrogel construct mechanical properties varying with culture time. Chondrocyte-seeded agarose constructs (2 mm thick) develop axial inhomogeneous mechanical properties with culture time. FS: free swelling and DL: dynamic loading (10% deformation, 1 Hz, 3 hours/daily, 20% FBS media).

Adopting a functional tissue engineering approach, optimized media conditions have been demonstrated (FIGS. 11A-11B) and applied dynamic deformational loading has been shown to promote mechanically functional engineered cartilage development of juvenile and adult chondrocytes, FIG. 13. Solute uptake by agarose hydrogel constructs and cartilage can be increased by a factor on the order of ten-fold with applied deformational loading compared to free-swelling controls. This effect is more pronounced for large solutes, as small solutes can diffuse more readily.

For purposes of this initial characterization, we studied a non-degradable hydrogel with microbubbles that ensures that changes to tissue properties can be attributed to cell activities only. Embodiments employ agarose hydrogel, a scaffold that has supported in vitro functional engineered cartilage development, shown good biocompatibility in canine preclinical model and tested in phase III clinical trials in Europe as a copolymer in a $3^{rd}$ generation autologous chondrocyte implantation. Embodiments may employ other candidate hydrogels, where the general benefits associated with hydrogel scaffolds including relative ease of uniform cell seeding, hydrophilic nature, ability to modulate polymer cross-linking density, as well as form various shapes and sizes is preserved.

Microbubble Methods

TABLE 1

Summary of Strategies for Construct Fabrication and Assessment Scaffold Fabrication Strategy

| | |
|---|---|
| Cell type | Juvenile bovine chondrocytes |
| Cell concentration | $30 \times 10^6$ cells/mL in hydrogel |
| Hydrogel | Agarose (2% weight/volume, Type VII, Sigma) |
| Microbubble shell | DSPC Lipid [16, 37] |
| Microbubble gas | Perfluorobutane (PFB) gas |
| Triggered gas dissolution | Hydrostatic pressure (preliminary data P2) |
| Microbubble size/conc. | Polydisperse via Accusizer |
| Microbubble dissolution | Wet weight change after triggered dissolution |
| Construct material properties | Equilibrium (EY) and Dynamic Modulus (G*) Dextran partition coefficient [2, 12] |
| Local material properties | Local EY, G* via digital image correlation microscope testing Local diffusivity via FRAP |
| Biochemical properties | DNA/wet weight, GAG/wet weight Collagen/wet weight (ELISA for type I-II) Histology/immunohistochemistry/polarized light [8, 19, 29] |

Microbubble strategies are summarized in Table 1. Cell Source: Articular chondrocytes will be enzymatically harvested from bovine carpo-metacarpal joints from freshly slaughtered 4-6 month old calves obtained from a local abattoir. Juvenile bovine chondrocytes are a well-established model for cartilage research and have demonstrated robust tissue growth and mechanically functional tissue development in our cartilage tissue engineering studies. After construct fabrication (described below), constructs will be maintained in culture for up to 56 days, with three-times weekly changes of chondrogenic growth medium (with 5 g/mL proline, 1% ITS+, 100 nM dexamethasone, 50 pg/mL ascorbate, and 10 ng/mL of TGF-3 for the first 2 weeks). During culture time, medium samples will be collected to analyze glycosaminoglycan (GAG) release in order to determine the relationship between GAG synthesis and retention in hydrogels with various microbubble concentrations. Collagen will also be monitored, but we anticipate negligible media levels of collagen since our enzymatic digestion studies indicate that collagen forms an interconnected network.

Construct Fabrication

Microbubbles can be created through sonication of distearoyl phosphatidylcholine (DSPC) lipid in perfluorobutane (PFB) gas. The resulting bubble mixture will be counted and sized (~0.5-10 um) using a technique to determine total gas volume. Gas volume fraction can be verified with construct buoyancy measurements. One volume of low-melt agarose (Type VII, Sigma) at 4% grams agarose/ml PBS will be mixed with an equal volume of cell suspension ($60 \times 10^6$ cells/ml of microbubble solution in media) at 37 C and gelled in sterile molds to yield a final cell concentration of $30 \times 10^6$ cells/ml in 2% w/v agarose with the desired concentration of microbubbles. Disks of 4 mm diameter will be cored out using a biopsy punch. Two-percent weight/volume agarose (Sigma, Type VII) has been shown to be more optimal than 1% and 3% w/v gels, with the 1% gels not retaining enough cell synthesized products and 3% gels providing too dense an environment to supply nutrients to central portions of the construct). As with most hydrogels, the increased gel concentration results in smaller tissue pores (and lower solute diffusivity).

Triggered Gas Dissolution

Microbubbles embedded in the agarose scaffold will be purged of gas through the application of hydrostatic pressure (~289 kPa) by compressing a sterile, capped syringe in an Instron testing rig (as shown in Section P2). The efficiency of gas removal will be quantified by the difference in wet weight before and after the application of hydrostatic pressure or by construct buoyancy measurements. Most of the gas can be expelled in this manner. Control disks will be subjected to the same experimental set up to account for any effects of the transient applied pressure, which is more than an order of magnitude lower than physiologic pressures during joint loading. An alternative strategy of gas removal is via vacuum degassing of the media.

Assessment of Construct Properties

Whole-construct mechanical properties (E and G*) will also be assessed via a custom testing device while construct-level diffusivity will be assessed by maintaining constructs in a bath of fluorescently labeled of 70 kDa dextran and reporting the uptake ratio (RU) of dextran captured inside the disk to that of the bathing solution, as previously described. Dextran is a hydrophilic polysaccharide available in a range of molecular weights (3 to 2000 kDa), and has low toxicity, is relatively inert and has good water solubility. Whole construct mechanical properties, the compressive Young's modulus and dynamic modulus (G*, a functional measure that reflects construct radial tensile properties and hydraulic permeability), will be determined as previously described. Local mechanical properties will be assessed via digital image correlation on a custom microscope testing device while local diffusivity will be assessed via fluorescence recovery after photobleaching (FRAP) measurements as previously described. Biochemical assessment of constructs will include GAG (DMMB assay), collagen (OHP assay), and ELISAs for type I and II collagen expressed as percentage wet weight (or DNA content via the Picogreen assay) will be quantified as routinely performed in the laboratory, along with histology (safranin-O, picosirius red, immunohistochemistry for collagen types, and polarized light for fiber organization).

Statistical Analyses

For a large effect size of 0.4, and significance at $p<0.05$, n=5 disks per time point yields a power greater than 0.91. We have designed our studies to yield n=6 samples for each test in case of sample loss. Post-hoc analyses was done using ANOVA with Tukey's post hoc test using Statistica (StatSoft, Oklahoma). Additionally, the strength of relationship between matrix characteristics (mechanical strength and diffusivity) and tissue growth will be analyzed using Pearson's correlation test. Each study was repeated at least twice using cells from independent cell preparations. Cells for an experiment are typically combined from wrist joints of 3-4 animals.

In embodiments, 10% peak-to-peak deformation is applied to scaffolds at 1 Hz without lift-off effects (i.e., separation of the loading platen from the sample). The microbubble stability may be increased via saturating the culture media with PFB gas to minimize gradients leading to gas efflux. Additionally, microbubble dissolution can be triggered at later points in culture.

Acellular microbubbles (polydisperse 0.5-10 μm) may be fabricated from vigorous shaking of distearoyl-phosphatidylcholine (DSPC) lipid in the presence of perfluorobutane (PFB) gas using a dental amalgamator. The resulting bubble mixture was suspended in PBS solution (A) or molten agarose (Type VII, Sigma) where cylindrical discs (Ø4×2.3 mm) were cast (A, inset; B), microbubble dissolution triggered (Section P2 below) and cultured for 28 days. Increasing microbubble concentration (0, 10, 20% v/v fraction) increased the turbidity of the constructs, making them appear more opaque (B) and decreased the construct modulus (C). The partition coefficient (defined as the ratio of construct/bath solute concentration determined using fluorescently-labeled 70 kDa dextran as described above) increases with microbubble concentration, indicating that microbubbles enhanced solute transport into the constructs, FIGS. 15A-15C.

Acellular microbubble constructs prepared in Section P1 above (20% v/v) were suspended in PBS in a 30 cc syringe (Becton Dickenson) with a luer plug at the syringe outlet, yielding a sealed fluid-filled chamber with a small volume of air below the syringe piston. The syringe was positioned axially on a table-top Instron device with the piston against the loading ram and a force (F) of 100 N applied (289 kPa). The construct was initially floating (near the piston) and as pressure was applied, the construct sank to the bottom as gas release from the microbubbles was triggered and their remnant pores became fluid-filled. Construct sinking is attributed to increased density associated with compression of the gas-filled microbubbles, thereby reducing its buoyancy. This buoyancy force is restored as the microbubbles become uncompressed. These observations demonstrate the feasibility of applying hydrostatic pressurization to microbubble incorporated hydro gel constructs in order to affect microbubble dissolution, FIGS. 16A-16B.

Microbubbles were fabricated as in Section P1 but with primary chondrocytes ($60 \times 10$ cells/mL) isolated from fresh bovine wrist joints and suspended in equal volume molten agarose (Type VII, Sigma), see FIG. 14. Cylindrical discs (Ø4×2.3 mm, $30 \times 10^6$ cells/mL) were cast, bubble dissolution triggered via hydrostatic pressure (Section P2 above) and cultured for 28 days in chemically-defined medium according to an optimized protocol. After 28 days in culture, constructs exhibited viable cells, and increased dynamic modulus and GAG content relative to microbubble-free control constructs. This study demonstrates the biocompatibility of microbubble infused hydro gel scaffolds and their ability to enhance cartilaginous tissue formation relative to control gels, FIGS. 17A-17C.

It will be appreciated that the controller described above can be implemented in hardware, software, or both. For example, a dynamic loading controller can be implemented, for example, using a processor configured to execute a sequence of programmed instructions. The processor can be for example, but not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as C++. The instructions can also comprise code and data objects provided in accordance with, for example, the Visual Basic™ language, or another object-oriented programming language. The sequence of programmed instructions and data associated therewith can be stored in a nontransitory computer-readable medium such as a computer memory or storage device which may be any suitable memory apparatus, such as, but not limited to ROM, PROM, EEPROM, RAM, flash memory, disk drive and the like. A computer program product can include the instructions and a computer-readable medium as described above.

Furthermore, the controller can be implemented as a single processor or as a distributed processor. Further, it should be appreciated that the steps mentioned above may be performed on a single or distributed processor. Also, the processes, modules, and sub-modules described in the various figures of and for embodiments above may be distributed across multiple computers or systems or may be co-located in a single processor or system. Exemplary structural embodiment alternatives suitable for implementing the controller described herein are provided below.

The controller described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a PLD, PLA, FPGA, PAL, or the like. In general, any process capable of implementing the functions or steps described herein can be used to implement embodiments of the method, system, or a computer program product (software program).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a VLSI design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of the mechanical, tissue engineering and/or computer programming arts.

Moreover, embodiments of the disclosed method, system, and computer program product can be implemented in software executed on a programmed general purpose computer, a special purpose computer, a microprocessor, or the like.

It is, therefore, apparent that there is provided, in accordance with the various embodiments disclosed herein, a microbubble devices, methods and systems.

While the invention has been described in conjunction with a number of embodiments, it is evident that many alternatives, modifications and variations would be or are apparent to those of ordinary skill in the applicable arts. Accordingly, Applicants intend to embrace all such alternatives, modifications, equivalents and variations that are within the spirit and scope of the appended claims.

The invention claimed is:

1. A cell culture apparatus comprising:
a first chemical treatment;
a hydrogel scaffold having gas-filled microbubbles and cells dispersed in the hydrogel, the hydrogel scaffold being floated on top of the first chemical treatment; and
a second chemical treatment applied to a top of the hydrogel scaffold.

2. The apparatus of claim 1, wherein the microbubbles have a shell comprising a protein, lipid or polymer.

3. The apparatus of claim 1, wherein the cells are chondrocyte cells.

4. The apparatus of claim 1, wherein the microbubbles are dispersed in the hydrogel before the hydrogel is polymerized.

5. The apparatus of claim 1, wherein the microbubbles have a volume density of more than 5%.

6. The apparatus of claim 1, wherein the microbubbles are less than 10 microns in diameter.

* * * * *